United States Patent
Vogt et al.

(10) Patent No.: US 11,771,484 B2
(45) Date of Patent: Oct. 3, 2023

(54) DEVICE FOR DISPENSING BONE CEMENT

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 412 days.

(21) Appl. No.: 17/077,567

(22) Filed: Oct. 22, 2020

(65) Prior Publication Data

US 2021/0113253 A1 Apr. 22, 2021

(30) Foreign Application Priority Data

Oct. 22, 2019 (EP) ..................................... 19204495

(51) Int. Cl.
*A61B 17/88* (2006.01)

(52) U.S. Cl.
CPC ...... *A61B 17/8816* (2013.01); *A61B 17/8822* (2013.01)

(58) Field of Classification Search
CPC ............ A61B 17/8816; A61B 17/8822; A61B 2017/0042; A61B 17/8802; A61B 17/8805; A61B 17/8819; A61B 17/8825
See application file for complete search history.

(56) References Cited

U.S. PATENT DOCUMENTS

| | | | |
|---|---|---|---|
| 4,338,925 A | | 7/1982 | Miller |
| 4,973,334 A * | | 11/1990 | Ziemann ............ A61B 17/8822 606/92 |
| 5,328,262 A | | 7/1994 | Lidgren et al. |
| 5,638,997 A | | 6/1997 | Hawkins et al. |
| 5,788,702 A * | | 8/1998 | Draenert ............ A61B 17/8811 606/92 |
| 6,547,432 B2 * | | 4/2003 | Coffeen ............... B01F 33/5011 366/195 |
| 6,796,987 B2 | | 9/2004 | Tague et al. |
| 9,010,586 B2 | | 4/2015 | Vogt et al. |
| 9,981,283 B2 * | | 5/2018 | Greter ................ B05C 17/00513 |
| 10,639,088 B2 | | 5/2020 | Vogt et al. |
| 10,765,463 B2 | | 9/2020 | Vogt et al. |
| 11,103,295 B2 | | 8/2021 | Vogt et al. |

(Continued)

FOREIGN PATENT DOCUMENTS

DE 4302230 A1 8/1993
DE 102017113126 A1 12/2018

(Continued)

*Primary Examiner* — Anu Ramana
(74) *Attorney, Agent, or Firm* — Dicke, Billig & Czaja, PLLC

(57) ABSTRACT

A device for dispensing a bone cement from a container, comprising a connecting element for reversibly connecting the device to the container, a rod-like dispensing element, which at least partially has an external thread, a switching system, which at least partially has a first internal thread, wherein the first internal thread can be coupled in a positive manner to the external thread in such a way that the dispensing element can be axially screwed into the container in a first coupled switching system position, and the dispensing element can be pushed freely axially into the container in a second decoupled switching system position.

14 Claims, 7 Drawing Sheets

(56) References Cited

U.S. PATENT DOCUMENTS

| | | |
|---|---|---|
| 2004/0204715 A1 | 10/2004 | Evans et al. |
| 2004/0260304 A1 | 12/2004 | Faccioli et al. |
| 2006/0036062 A1* | 2/2006 | Ramakrishna ............ C12P 7/56 |
| | | 528/354 |
| 2013/0079786 A1* | 3/2013 | Bonnin .............. A61B 17/8822 |
| | | 606/94 |
| 2017/0173624 A1* | 6/2017 | Greter ............... B05C 17/00513 |

FOREIGN PATENT DOCUMENTS

| | | |
|---|---|---|
| EP | 0861117 A1 | 9/1998 |
| EP | 3395274 A1 | 10/2018 |
| EP | 3320869 B1 | 5/2019 |
| EP | 2457531 B1 | 6/2019 |
| WO | 97/18031 A1 | 5/1997 |
| WO | 2019/200091 A1 | 10/2019 |

\* cited by examiner

DEVICE FOR DISPENSING BONE CEMENT

CROSS-REFERENCE TO RELATED APPLICATION

This Utility Patent Application claims priority to European Application No. 19204495.6 filed on Oct. 22, 2019, which is incorporated herein by reference.

TECHNICAL FIELD

One aspect relates to a device for dispensing a bone cement from a container and one provide a method, by which a bone cement can be dispensed from a container.

BACKGROUND

Considerable efforts are made to show a device and method for dispensing bone cement, by which bone cement can be applied easily, safely, and cost-efficiently during orthopaedic surgeries, in particular while fixing artificial hip and knee joints with bone material.

The bone cement is usually provided in containers and is dispensed from the containers by using dispensing guns. Dispensing guns of this type are described, for example, in U.S. Pat. Nos. 5,638,997 B2 and 4,338,925 A. The dispensing guns have a trigger mechanism, whereby the actuation of a trigger drives a dispensing element, which dispenses the bone cement from the container. A disadvantage of dispensing guns of this type is the difficulty of dispensing exact amounts of bone cement from the container because the amount of the bone cement is usually delivered by complete trigger strokes or at least in discrete volume units imposed by the mechanics of the dispensing gun. In addition, high costs are incurred when using dispensing guns of this type, which result from the high acquisition costs on the one hand as well as from the necessary disinfection steps for reusing the expensive application guns.

On the market, there is the desire to improve and reduce the costs of devices for dispensing bone cement.

A device for dispensing bone cement is described in U.S. Pat. No. 6,796,987 B2, which has a dispensing element, which is provided with an external thread, for dispensing a bone cement from a container by using a rotational movement. For this purpose, the external thread couples on one side to a section of an internal thread of a switching element, whereby the internal thread is pushed against the external thread using a spring. Due to a constant pressure against the switching system, the internal thread can be decoupled from the external thread, which allows for an axially free shifting of the dispensing element within the device.

A disadvantage of the device is that the axially free shifting is possible only when maintaining a constant pressure against the switching system. This makes it more difficult for the surgeon to operate the device, because one hand is tied by the actuation of the switching system.

A further disadvantage of the device is the one-sided coupling of the external thread to the internal thread. This leads to a one-sided material stress and thus increases the susceptibility of break-related failures of the device.

A further disadvantage of the device is a weak mechanical coupling between external thread and internal thread, which is determined only by the tension force of the spring. In one embodiment in the case of highly viscous bone cements, the tension force of the spring is not sufficient to dispense the bone cement. Instead of being continuously screwed in, the dispensing element is instead pushed away, and the internal thread is thus decoupled from the external thread.

In addition, the device includes many movable components, so that the risk of malfunctions, in particular caused by the spring, is increased.

For these and other reasons there is a need for the present embodiment.

SUMMARY

One aspect relates to a device for dispensing a bone cement from a container, including a connecting element for reversibly connecting the device to the container, a rod-like dispensing element, which at least partially has an external thread, a switching system, which at least partially has a first internal thread, wherein the first internal thread can be coupled in a positive manner to the external thread in such a way that the dispensing element can be axially screwed into the container in a first coupled switching system position, and the dispensing element can be pushed freely axially into the container in a second decoupled switching system position. One embodiment furthermore relates to a method for dispensing a bone cement from a container by using a device including a connecting element for reversibly connecting the device to the container, a rod-like dispensing element, which at least partially has an external thread, a switching system, which at least partially has a first internal thread, wherein the first internal thread can be coupled in a positive manner to the external thread in such a way that the dispensing element can be axially screwed into the container in a first coupled switching system position, and the dispensing element can be pushed freely axially into the container in a second decoupled switching system position.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
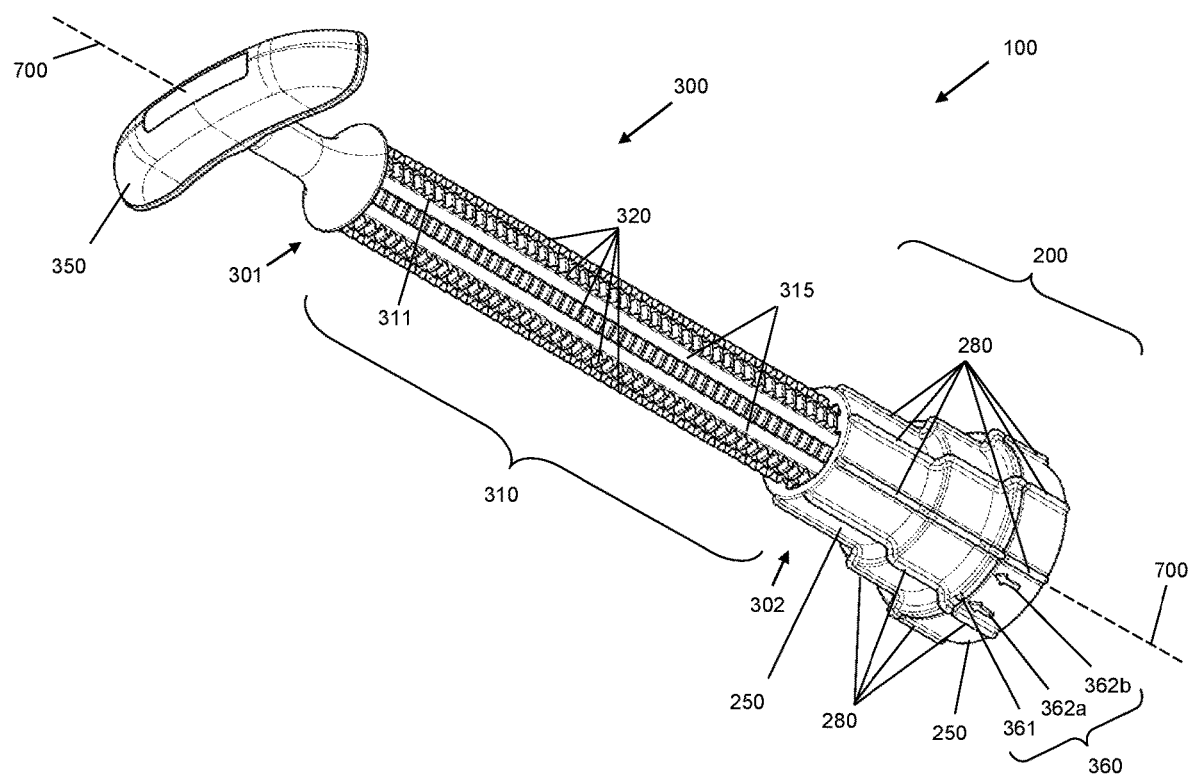
FIG. 1 illustrates a device for dispensing a bone cement from a container.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

Embodiments

It is an object of the one embodiment to at least partially overcome one or several of the disadvantages resulting from the prior art.

One embodiment is based on the goal of providing devices for dispensing a bone cement from a container, which are easy to handle and cost-efficient and which have a high mechanical stability. The device is to be suitable for containers, in which a bone cement is collected at one end of the container prior to the dispensing under the effect of negative pressure, as well as for containers, in which a bone cement is distributed in an undefined manner over an internal volume of the container prior to the dispensing. The device is to keep the amount of work for the user as small as possible and is to provide for the quickest possible start of the dispensing for containers, in which a bone cement is collected at an end, in one embodiment a dispensing end, prior to the dispensing, for example under the effect of negative pressure.

It is a further object of one embodiment to provide a method, by which a bone cement can be dispensed from a container, by which at least a part of the already described embodiments is at least partially solved.

The features of the independent claims make a contribution to at least partially fulfilling at least one of the above-mentioned objects. The dependent claims provide embodiments, which contribute to at least partially fulfilling at least one of the embodiments.

[1] A device for dispensing a bone cement from a container,
including a connecting element for reversibly connecting the device to the container, a rod-like dispensing element, which at least partially has an external thread,
a switching system, which at least partially has a first internal thread, wherein the first internal thread can be coupled in a positive manner to the external thread in such a way that
the dispensing element can be axially screwed into the container in a first coupled switching system position, and the dispensing element can be pushed freely axially into the container in a second decoupled switching system position, characterised in that
the first internal thread encompasses the dispensing element in a sleeve-like manner, and the switching system can be reversibly shifted between the first switching system position and the second switching system position by using a rotatory movement about a longitudinal axis of the dispensing element.

[2] The device according to embodiment 1, characterised in that the switching system has a first hollow cylinder, which has the first internal thread, and a second hollow cylinder, which is axially connected to the first hollow cylinder,
wherein the first hollow cylinder and the second hollow cylinder are connected in such a way that the switching system can be reversibly shifted between the first switching system position and the second switching system position by using a rotatory movement of the first hollow cylinder in the opposite direction against the second hollow cylinder about the longitudinal axis.

[3] The device according to embodiment 2, characterised in that the second hollow cylinder at least partially has a second internal thread, and the external thread has at least one external thread groove, which runs along the longitudinal axis,
the first internal thread has at least one first internal thread groove, which runs along the longitudinal axis, and
the second internal thread has at least one second internal thread groove, which runs along the longitudinal axis.

[4] The device according to embodiment 3, characterised in that the at least one external thread groove divides the external thread into external thread sections, the at least one first internal thread groove divides the first internal thread into first internal thread sections, and the at least one second internal thread groove divides the second internal thread into second internal thread sections along the longitudinal axis.

[5] The device according to embodiment 4, characterised in that a radial extension of the at least one external thread groove, of the at least one first internal thread groove, and of the at least one second internal thread groove, is equal to or larger than a radial extension of the external thread section, of the first internal thread section, and of the second internal thread section.

[6] The device according to any one of the embodiments 3 to 5, characterised in that the external thread, the first internal thread, and the second internal thread have an essentially identical angle of inclination.

[7] The device according to any one of the embodiments 3 to 6, characterised in that the external thread, the first internal thread, and the second internal thread each have an identical number of external thread grooves, first internal thread grooves, and second internal thread grooves, each including the essentially identical radial extension.

[8] The device according to any one of the embodiments 3 to 7, characterised in that the at least one first internal thread groove and the at least one second internal thread groove are located on an essentially common axis in the second switching system position.

[9] The device according to embodiment 8, characterised in that the at least one first internal thread groove and the at least one second internal thread groove are oriented to the external thread, in one embodiment are located on a common axis, in such a way in the second switching system position that the external thread can be pushed axially freely into the first internal thread groove and the second internal thread groove, in order to push the dispensing element freely axially into the container.

[10] The device according to any one of the embodiments 3 to 9, characterised in that the at least one first internal thread groove and the at least one second internal thread groove are not located on a common axis in the first switching system position.

[11] The device according to embodiment 10, characterised in that the at least one first internal thread groove and the at least one second internal thread groove are not located on a common axis in the first switching system position, so that the external thread couples to one another with the first internal thread and the second internal thread in such a way that the dispensing element can be screwed axially into the container.

[12] The device according to any one of the preceding embodiments, characterised in that the device is made of plastic, in one embodiment of a compostable plastic, in one embodiment of a glass fibre-reinforced plastic, metal, or of a combination of plastic, in one embodiment of a compostable plastic, in one embodiment of a glass fibre-reinforced plastic and metal.

[13] The device according to any one of the preceding embodiments, characterised in that the first hollow cylinder encompasses the connecting element.

[14] A method for dispensing a bone cement from a container by using a device including
a connecting element for reversibly connecting the device to the container,
a rod-like dispensing element, which at least partially has an external thread,
a switching system, which at least partially has a first internal thread, wherein the first internal thread can be coupled in a positive manner to the external thread in such a way that
the dispensing element can be axially screwed into the container in a first coupled switching system position, and
the dispensing element can be pushed freely axially into the container in a second decoupled switching system position,
at least including the steps of
a) connecting the device to the container by using the connecting element;
b) moving the switching system into the second switching system position;
c) axial shifting of the dispensing element into the container;
d) moving the switching system into the first switching system position by using a rotatory movement about a longitudinal axis of the dispensing element;
e) dispensing the bone cement from the container by screwing the dispensing element into the container.

[15] The method according to embodiment 14, characterised in that the rotatory movement in step d) shifts a first hollow cylinder of the switching system against a second hollow cylinder of the switching system in a rotatory manner.

[16] The method according to embodiment 14 or 15, characterised in that the first hollow cylinder has the first internal thread, and the second hollow cylinder has a second internal thread,
wherein the external thread includes at least one external thread groove, the first internal thread includes at least one first internal thread groove, and the second internal thread includes at least one second internal thread groove, and the at least one external thread groove divides the external thread into external thread sections,
the at least one first internal thread groove divides the first internal thread into first internal thread sections, and
the at least one second internal thread groove divides the second internal thread into second internal thread sections, each along the longitudinal axis, and wherein the at least one first internal thread groove and the at least one second internal thread groove are arranged on an essentially common axis in the second switching system position, so that the external thread sections are shifted into the container along the common axis in step c).

In the present description, range specifications also include the values mentioned as limits. A designation of the type "in the range of X to Y" with regard to a variable A thus means that A can take on the values X, Y and values between X and Y. Ranges of the type "up to Y", which are limited on one side, for a variable A, accordingly mean Y and less than Y as values.

Described features can be combined with the term "essentially". The term "essentially" is to be understood such that under actual conditions and production techniques, a mathematically exact interpretation of concepts, such as "overlap", "perpendicular", "diameter", or "located on one axis" can never be specified exactly, but only within certain production-related error tolerances. For example, "essentially parallel axes" draw an angle of 85 degrees to 95 degrees relative to one another, and "essentially identical volumes" include a deviation of up to 5% by volume. A "device consisting essentially of plastic" includes a plastic content of, for example, $\geq 95$ to $\leq 100\%$ by weight.

A first subject matter of the embodiment relates to a device for dispensing a bone cement from a container, including
a connecting element for reversibly connecting the device to the container,
a rod-like dispensing element, which at least partially has an external thread,
a switching system, which at least partially has a first internal thread,
wherein the first internal thread can be coupled in a positive manner to the external thread in such a way that the dispensing element can be axially screwed into the container in a first coupled switching system position, and
the dispensing element can be pushed freely axially into the container in a second decoupled switching system position,
characterised in that
the first internal thread encompasses the dispensing element in a sleeve-like manner, and
the switching system can be reversibly shifted between the first switching system position and the second switching system position by using a rotatory movement about a longitudinal axis of the dispensing element.

The device has a connecting element for reversibly connecting the device to the container, in one embodiment to an open axial end of the container. The connecting element connects the device and the container in such a way that the device and the container are located on a common axis. The connecting element can be embodied in different ways for reversibly connecting the device to a container. In one embodiment, the connecting element is embodied as internal thread for establishing a connection to a corresponding external thread of the container. In a further embodiment, the connecting element is embodied as one or several engagement hooks, which engage with corresponding depressions at the container. In one embodiment, the device and the container are connected to one another via a bayonet closure.

The device has a rod-like dispensing element for dispensing the bone cement from the container. For this purpose, the dispensing element is axially inserted into the open end of the container, which is connected to the connecting element, which leads to a dispensing of the bone cement from a dispensing end located opposite the open end of the container in response to continued insertion. To be able to be capable of being inserted into the container, the dispensing element has an outer diameter, which essentially is equal to or smaller than an inner diameter of the container, as well as a length, which is sufficient to completely dispense the bone cement from the container.

The dispensing of the bone cement from the container by inserting the dispensing element can be realised in different ways. In one embodiment, the dispensing element acts on the bone cement by direct physical contact. For this purpose, the dispensing element has an axial end, which faces the dispensing side of the container and which has a diameter, which essentially corresponds to the inner diameter of the container. In response to a shifting into the container, an axial end of the dispensing element of this type cooperates with an inner wall of the container in such a way that the bone cement is pressed out of the container. In a further embodiment, the dispensing element acts on a dispensing piston, which is located in the container and which is located spatially between the dispensing element and the bone cement. The dispensing piston has a dispensing piston diameter, which essentially corresponds to the inner diameter of the container. An end of the dispensing element facing the dispensing piston shifts the dispensing piston in the direction of the dispensing side of the container and thus presses the bone cement out of the container with continued insertion of the dispensing element into the container.

The device has a switching system. The switching system serves to control the movement type of the dispensing element into the container. For this purpose, the switching system has two switching system positions, whereby a first switching system position provides only a rotational movement, and a second switching system position provides a pushing movement of the dispensing element into the container.

To control the movement type of the dispensing element by the setting into one of the two switching system positions, the dispensing element has at least partially an external thread, and the switching system has at least partially a first internal thread. In the first switching system position, the external thread and the first internal thread are coupled to one another and cooperated in a positive and/or non-positive manner in such a way that a relative rotational movement of dispensing element and switching system relative to one another screws the dispensing element into the container. In the first switching system position, the external thread and the first internal thread cooperate in such a way that an introduction of the dispensing element into the container can take place only via a rotational movement. To facilitate the rotational movement for the user of the device, the dispensing element can have a screwing means, for example an elongate handle, which is adapted to the palm of a hand. In the second switching system position, the external thread and the first internal thread are decoupled, so that the dispensing element can be moved freely axially into the container by using a pushing movement. In the second switching system position, a rotational movement is not necessary for introducing the dispensing element into the container.

The first internal thread encompasses the dispensing element and thus also the external thread in a sleeve-like manner. In a sleeve-like manner means that the first internal thread encompasses the entire cross-sectional circumference of the dispensing element, and not only a partial area thereof, in the first switching system position as well as in the second switching system position. An advantage of the sleeve-like design of the internal thread is a high mechanical stability of the device, which is required in one embodiment when screwing in the dispensing element in the first switching system position by dispensing a highly viscous bone cement. The firm sleeve-like encompassing prevents an unintentional decoupling of external thread and first internal thread, as it would only be possible in the case of sectional coupling of external thread and internal thread. A further advantage is the even mechanical stress of the dispensing element, which extends over the entire cross-sectional surface of the dispensing element and thus contributes to the mechanical stability of the device.

The switching system can be reversibly shifted between first switching system position and second switching system position by using a rotatory movement about a longitudinal axis of the dispensing element. The switching system remains in the set switching system position, as long as no external force acts on the switching system, for example by the user of the device. The device does not have a restoring element, such as a spring, for example, which moves the switching system independently and without external force, such as, for example, by the user of the device, from the one switching system position into the other switching system position. An advantage of a switching system of this type is that the user does not have to continuously apply force against a restoring element, such as a spring, for example, and thus has both hands free for handling the device and the container. This makes it easier for the user to handle the device. A further advantage is that due to the small number of required, in one embodiment mobile components, such as, for example, a restoring element, a switching system of this type has a high mechanical stability and thus has a reduced risk of malfunctions.

An embodiment of the device is characterised in that the switching system has a first hollow cylinder, which has the first internal thread, and a second hollow cylinder, which is axially connected to the first hollow cylinder, wherein the first hollow cylinder and the second hollow cylinder are connected in such a way that the switching system can be reversibly shifted between the first switching system position and the second switching system position by using a rotatory movement of the first hollow cylinder in the opposite direction against the second hollow cylinder about the longitudinal axis.

The switching system has a first hollow cylinder and a second hollow cylinder. A hollow cylinder is to be understood as a tubular element, which includes an interior and an element wall surrounding the interior. Perpendicular to a longitudinal axis, the hollow cylinder has a cross-section, wherein the cross-section can assume different shapes. The cross section can be, for example, oval, square, pentagonal, hexagonal, irregular, or circular. A circular cross-section is preferred for the user due to the easy handling, whereby the first hollow cylinder and/or the second hollow cylinder can have cross-sections of different sizes compared with one another as well as within a hollow cylinder. In one embodiment, it is preferred that the first hollow cylinder and/or the second hollow cylinder have structures on an outer side, which facilitate the rotation of the first hollow cylinder in the opposite direction against the second hollow cylinder for the user. In one embodiment, the first hollow cylinder and/or the second hollow cylinder have nubs on the respective outer side. In one embodiment the first hollow cylinder and/or the second hollow cylinder have at least one bead, which runs along the longitudinal axis of the device. Beads are preferred, because the grip of the outer surface of the hollow cylinder is increased, in one embodiment when wearing gloves under surgical conditions. On the one hand, this facilitates the moving of the switching system into the first switching system position and the second switching system position and lowers the user's risk of slipping with one or both hands during the rotatory movement.

The first hollow has the internal thread and is axially connected to the second hollow cylinder in such a way that a rotation of the two hollow cylinders in the opposite direction about the longitudinal axis is possible. The first hollow cylinder and the second hollow cylinder can be connected to one another in different ways to provide a rotation in the opposite direction. Threads, plug connections, or bayonet closures are examples for possible connection types.

The rotatability of the first hollow cylinder in the opposite direction against the second hollow cylinder can be embodied in different ways. In one embodiment, the first hollow cylinder and the second hollow cylinder can be rotated against one another in a direction of rotation to any extent, and can move the switching system alternately into the first switching system position and the second switching system position in response to this continued rotation in the opposite direction. In one embodiment the first hollow cylinder and the second hollow cylinder cannot be rotated against one another in a direction of rotation to any extent, but the rotatability in a direction of rotation is limited by a stop. In one embodiment, the rotatability is limited by exactly one stop, so that the switching system can be moved into the first switching system position by using a rotation of the first hollow cylinder and of the second hollow cylinder in the opposite direction in a direction of rotation all the way to this stop, and can be moved into the second switching system position by using a rotation in the opposite direction all the way to this stop. In one embodiment the switching system has two stops, so that a rotation of the first hollow cylinder and the second hollow cylinder in the opposite direction all the way to the first stop moves the switching system into the first switching system position, and a rotational movement in the opposite direction all the way to the second stop moves the switching system into the second switching system position. Due to the presence of at least one stop, the user obtains a clear physical response whether a switch-over of the switching system position has taken place. The user can also read the respectively set switching system position by optical markings, for example by colour markings, accentuations, or notches, at the first hollow cylinder and/or at the second hollow cylinder.

The first hollow cylinder and the second hollow cylinder can cooperate in different ways to reversibly switch the switching system between the first switching system position and the second switching system position by using a rotatory movement of the first hollow cylinder in the opposite direction against the second hollow cylinder about the longitudinal axis of the dispensing element.

An embodiment of the device is characterised in that the second hollow cylinder at least partially has a second internal thread, and the external thread of the dispensing element has at least one external thread groove, which runs along the longitudinal axis, the first internal thread has at least one first internal thread groove, which runs along the longitudinal axis, and the second internal thread has at least one second internal thread groove, which runs along the longitudinal axis.

In this embodiment, the first hollow cylinder as well as the second hollow cylinder are arranged around the dispensing element in a sleeve-like manner, so that the first internal thread and the second internal thread can cooperate in a positive and/or non-positive manner with the external thread. In one embodiment, the second internal thread essentially adjoins the first internal thread directly axially, so that the second internal thread represents an extension of the first internal thread. In a further embodiment, there is a gap between first internal thread and second internal thread, whereby the gap has a smaller axial extension than the external thread, so that the external thread can cooperate in a positive and/or non-positive manner at least with the first internal thread or the second internal thread at any time.

In the first switching system position, the first internal thread and/or the second internal thread cooperate in a positive and/or non-positive manner with the external thread. The external thread is thus always coupled at least to one of the two internal threads, and an axial introduction of the dispensing element into the container is possible only by using a rotational movement.

To decouple the external thread from the first internal thread and second internal thread in the second switching system position, the external thread has at least one external thread groove, the first internal thread has at least one first internal thread groove, and the second internal thread has at least one second internal thread groove. The respective thread grooves in each case run along the longitudinal axis of the dispensing element. The at least one first internal thread groove and the at least one second internal thread groove in each case extend over the entire axial extension of the first internal thread and of the second internal thread. The at least one external thread groove extends over the external thread at least as long as the dispensing element has to be introduced into the container in order to completely dispense the bone cement, whereby the extension encompasses an end of the dispensing element facing the container. The height of the thread flanks of the respective threads is reduced along the respective thread grooves. In one embodiment, the height of the thread flanks is reduced to zero, so that the respective thread has a complete interruption along the thread groove. A reduction of the height of the thread flank to zero means that the thread groove is located at a height including a lowest notch of a thread turn of the respective thread. In a further embodiment, the respective thread is not reduced to zero along the thread groove, but, compared to the thread flank outside of the thread groove, it is only reduced, for example to 50% of the height. In a further embodiment, the respective thread is reduced beyond the deepest notch of the thread turn along the thread groove.

A positive and/or non-positive interaction between the external thread and the first internal thread and/or the second internal thread does not take place in the respective area of the thread grooves. In the second switching system position, the at least one first internal thread groove and the at least one second internal thread groove are arranged relative to one another in such a way that the dispensing element can be pushed freely axially into the container.

An embodiment of the device is characterised in that the at least one external thread groove divides the external thread into external thread sections, the at least one first internal thread groove divides the first internal thread into first internal thread sections, and the at least one second internal thread groove divides the second internal thread into second internal thread sections along the longitudinal axis.

A thread section is an area of the respective thread including a maximal height of the respective thread flank, which is not traversed by a thread groove. The thread sections are embodied in such a way that a positive and/or non-positive cooperation of the external thread sections as well as of the first internal thread sections and/or of the second internal thread sections is possible. In the first switching system position, the external thread sections cooperate in a positive and/or non-positive manner with the first internal thread sections and/or the second internal thread sections, so that the dispensing element can only be screwed into the container by using a rotational movement. In the second switching system position, the at least one first internal thread groove and the at least one second internal thread groove is arranged relative to one another in such a way that the external thread sections can be shifted freely axially in the device along the first internal thread groove and the second internal thread groove.

To provide for a free axial shifting of the dispensing element into the container, an embodiment of the device is characterised in that a radial extension of the at least one external thread groove, of the at least one first internal thread groove, and of the at least one second internal thread groove, is equal to or larger than a radial extension of the external thread section, of the first internal thread section, and of the second internal thread section.

A free axial shifting of the external thread sections along the axial extension of the first internal thread groove and of the second internal thread groove and simultaneously a free axial shifting of the first internal thread sections and of the second internal thread sections along the axial extension of the external thread groove is thus possible.

To provide for a positive and/or non-positive cooperation of external thread, in one embodiment from the external thread sections, with the first internal thread and/or the second internal thread, in one embodiment with the first internal thread sections and/or the second internal thread sections, in the first switching system position, an embodiment of the device is characterised in that the external thread, the first internal thread, and the second internal thread, in one embodiment the external thread sections, the first internal thread sections, and the second internal thread sections, have an essentially identical angle of inclination.

The external thread as well as the first internal thread and the second internal thread can have a different number of respective thread grooves, and associated therewith, a different number of respective thread sections, including different radial expansions. So that a free axial shifting of the dispensing element into the container is possible in the second switching system position, however, the respective threads have to be capable of being spatially arranged in such a way that a shifting of the external thread sections along the first internal thread groove and the second internal thread groove, and simultaneously a shifting of the first internal thread sections and of the second internal thread sections along the external thread grooves is possible.

An embodiment of the device is characterised in that the external thread, the first internal thread, and the second internal thread each have an identical number of external thread grooves, first internal thread grooves, and second internal thread grooves, each including the essentially identical radial extension.

An advantage of this embodiment is a high mechanical stability of the device and an even force distribution in response to dispensing the bone cement to the respective threads.

In one embodiment, the respective thread sections have the same radial extension as the respective thread grooves. In one embodiment the respective thread sections have a small radial extension, for example up to 1 mm smaller, than the respective thread grooves, whereby the free axial shifting of the dispensing element in the second switching system position is facilitated for the user due to a simplified spatial positioning of the dispensing element within the switching system.

The respective threads have, for example, two to twelve respective thread grooves, whereby the higher the number of the thread grooves, the more evenly a force is distributed to the respective threads. The more even force distribution results in an increased mechanical stability of the device. As the number of thread grooves increases, the difficulty of the matching spatial positioning of the dispensing element within the switching system increases as well. A thread groove number of six to ten, in one embodiment of eight thread grooves, has turned out to be a good compromise between high mechanical stability and simplicity of the spatial positioning.

An embodiment of the device is characterised in that the at least one first internal thread groove and the at least one second internal thread groove are located on an essentially common axis in the second switching system position.

A decoupling of external thread and first internal thread as well as of second internal thread, and thus a complete reversible insertion of the dispensing element into the container is thus possible without rotations about the longitudinal axis of the dispensing element, which facilitates the operation of the device for the user.

To decouple the external thread from the first internal thread and from the second internal thread, and to thus freely axially shift the dispensing element, an embodiment of the device is characterised in that the at least one first internal thread groove and the at least one second internal thread groove are oriented to the external thread, in one embodiment are located on an essentially common axis, in such a way in the second switching system position that the external thread can be pushed axially freely into the first internal thread groove and the second internal thread groove, in order to push the dispensing element freely axially into the container.

An embodiment of the device is characterised in that the at least one first internal thread groove and the at least one second internal thread groove are not located on a common axis in the first switching system position.

The external thread is thus connected in a positive and/or non-positive manner to the first internal thread and/or to the second internal thread, and the dispensing element can consequently only be moved by screwing into the container by using rotational movement.

To couple the external thread to the switching system, an embodiment of the device is characterised in that the at least one first internal thread groove and the at least one second internal thread groove are not located on a common axis in the first switching system position, so that the external thread couples with the first internal thread and the second internal thread in such a way that the dispensing element can be screwed axially into the container.

As a result, the first internal thread, in one embodiment the at least one first internal thread section, and/or the second internal thread, in one embodiment the at least one second internal thread section, cooperate in a positive and/or non-positive manner with the external thread, in one embodiment with the at least one external thread section, and are thus coupled to one another.

The device can be made of different materials or material combinations.

An embodiment of the device is characterised in that the device is made of plastic, in one embodiment of a compostable plastic, in one embodiment of a glass fibre-reinforced plastic, metal, or of a combination of plastic, in one embodiment of a compostable plastic, in one embodiment of a glass fibre-reinforced plastic and metal.

Due to the low costs and simple production process, plastics are preferred. The use of plastics provides for an economically sustainable one-time usage of the device, whereby, in addition to the already low acquisition costs, the cost-intensive disinfection steps for the reuse can be forgone. To increase the mechanical stability of the plastics, plastics, which are in one embodiment reinforced with glass fibres, are preferred. In one embodiment compostable plastics are preferred for ecological reasons. Polyamides, such as polyamide 12 or polyamide 6, and polyimides, are examples for plastics.

To impart individual, selective sections of the device with a particularly high mechanical strength, these sections can be made of metals. Iron, steel, copper, or aluminium, or alloys of these metals are examples for the metals.

The connecting element can be attached at different points of the device.

Due to the simple handling and the smallest possible number of components, an embodiment of the device is characterised in that the first hollow cylinder encompasses the connecting element.

A second embodiment relates to a method for dispensing a bone cement from a container by using a device including a
- connecting element for reversibly connecting the device to the container,
- a rod-like dispensing element, which at least partially has an external thread,
- a switching system, which at least partially has a first internal thread,
- wherein the first internal thread can be coupled in a positive manner to the external thread in such a way that
- the dispensing element can be axially screwed into the container in a first coupled switching system position, and
- the dispensing element can be pushed freely axially into the container in a second decoupled switching system position,
- at least including the steps of
  - a) connecting the device to the container by using the connecting element;
  - b) moving the switching system into the second switching system position;
  - c) axial shifting of the dispensing element into the container;
  - d) moving the switching system into the second switching system position by using a rotatory movement about a longitudinal axis of the dispensing element;
  - e) dispensing the bone cement from the container by screwing the dispensing element into the container.

A further embodiment of the method is characterised in that the rotatory movement in step d) shifts a first hollow cylinder of the switching system against a second hollow cylinder of the switching system in a rotatory manner. An advantage of the described method is that the user does not have to hold the device, in one embodiment the switching system, in the second switching system position by continuously applying force against a restoring element, such as a spring, for example. The user thus has both hands free for handling the device, in one embodiment for axially shifting the dispensing element into the container, which makes it easier to perform the method.

A further embodiment of the method is characterised in that the first hollow cylinder has the first internal thread, and the second hollow cylinder has a second internal thread,
- wherein the external thread includes at least one external thread groove,
- the first internal thread includes at least one first internal thread groove, and
- the second internal thread includes at least one second internal thread groove, and the at least one external thread groove divides the external thread into external thread sections,
- the at least one first internal thread groove divides the first internal thread into first internal thread sections, and
- the at least one second internal thread groove divides the second internal thread into second internal thread sections, each along the longitudinal axis, and wherein the at least one first internal thread groove and the at least one second internal thread groove are arranged on an essentially common axis in the second switching system position, so that the external thread sections are shifted into the container along the common axis in step c).

Due to the fact that the at least one first internal thread groove and the at least one second internal thread groove are located on an essentially common axis in the second switching system position, the axial shifting of the dispensing element can be performed in step c) in that the user simply pushes into the container. The user thereby has both hands free, which makes it easier to perform the method. In addition, the user does not have to apply an additional force caused by the device, such as, for example, pushing against a restoring element, in order to move the dispensing element to the desired position. If the dispensing element is at the desired position within the container, the user moves the switching system into the first switching system position by using a further rotatory movement of the first hollow cylinder against the second hollow cylinder. In the second switching system position, the first internal thread groove and the second internal thread groove are not located on a common axis, but the external thread sections cooperate in a positive and/or non-positive manner with the first internal thread sections and/or the second internal thread sections, so that a continued axial shifting by exerting pressure on the dispensing element is no longer possible. A continued movement of the dispensing element into the container, in one embodiment for dispensing the bone cement, is attained by screwing the dispensing element into the container. The screw-in can be performed until the desired amount of bone cement has been applied. The switching system in one embodiment is to be moved from the first switching system position into the second switching system position as soon as the dispensing element is inserted into the container to the extent that the dispensing of the bone cement begins. The force from the user increases at that point in time due to the viscosity of the bone cement, whereby a dispensing is facilitated for the user by using screwing in. In addition, the screwing in facilitates the exact metering of the bone cement as compared to the dispensing by using insertion. The insertion in the second switching system position has the advantage that it can take place quickly. This is advantageous in one embodiment during time-critical surgeries and due to the quick hardening of the bone cement, for example within 5 minutes.

The device is characterised in that it can dispense a bone cement from a container. According to one embodiment, a bone cement is understood to be a substance, which is suitable to establish a stable connection between artificial joints, such as, for example, hip and knee joints, and bone material in the field of medical technology. Bone cements are in one embodiment preferably polymethylmethacrylate bone cements (PMMA bone cements). PMMA bone cements have already been used for a long time in medical applications and are based on the works of Sir Charnley (see Charnley, J. Anchorage of the femoral head prosthesis of the shaft of the femur. J. Bone Joint Surg. 1960; 42, 28-30.). PMMA bone cements can thereby be made of a bone cement powder as first starting component, and a monomer liquid as second starting component. In the case of a suitable composition, the two starting components can be stable in storage separately from one another. When bringing the two starting components into contact, a plastically deformable bone cement, which is also referred to as bone cement paste, is created by swelling the polymer components of the bone cement powder. A polymerisation of the monomer is thereby initiated by using radicals. The viscosity of the bone cement increases with continuous polymerisation of the monomer, until the bone cement hardens completely. According to one embodiment, a bone cement powder is understood to be a powder, which includes at least one particulate polymethylmethacrylate and/or a particulate polymethylmethacrylate copolymer. Styrene and/or methyl acrylate are examples for copolymers. In an embodiment, the bone cement powder can additionally include a hydrophilic additive, which supports the distribution of the monomer liquid within the bone cement powder. In a further embodiment, the bone cement powder can additionally include an initiator, which initiates the polymerisation. In a further embodiment, the bone cement powder can additionally include a radiopaque. In yet a further embodiment, the bone cement powder can additionally include pharmaceutically active substances, such as, for example, antibiotics.

The bone cement powder in one embodiment includes at least one particulate polymethylmethacrylate and/or a particulate polymethylmethacrylate copolymer, an initiator, and a radiopaque, or consists of these components. In one embodiment the bone cement powder includes at least one particulate polymethylmethacrylate and/or a particulate polymethylmethacrylate copolymer, an initiator, a radiopaque, and a hydrophilic additive, or consist of these components. In one embodiment, the bone cement powder includes at least one particulate polymethylmethacrylate and/or a particulate polymethylmethacrylate copolymer, an initiator, a radiopaque, a hydrophilic additive, and an antibiotic, or consists of these components.

According to one embodiment, the particle size of the particulate polymethylmethacrylate and/or of the particulate polymethylmethacrylate copolymer of the bone cement powder can correspond to the sieve fraction of less than 150 µm, in one embodiment less than 100 µm.

According to one embodiment, the hydrophilic additive can be embodied in a particulate and/or fibrous manner. In a further embodiment, the hydrophilic additive can be of low solubility, in one embodiment insoluble, in methylmethacrylate. In a further embodiment, the hydrophilic additive can have an absorption capacity of at least 0.6 g of methylmethacrylate per gram of hydrophilic additive. In a further embodiment, the hydrophilic additive can have a chemical substance including at least one OH group. It can thereby in one embodiment be provided that the hydrophilic additive has covalently bound OH groups at its surface. Additives selected from the group including cellulose, oxycellulose, starch, titanium dioxide and silicon dioxide can be examples for preferred hydrophilic additives of this type, whereby pyrogenic silicon dioxide is preferred in one embodiment. In an embodiment, the particle size of the hydrophilic additive can correspond to the sieve fraction of less than 100 µm, in one embodiment less than 50 µm, and in one embodiment less than 10 µm. The hydrophilic additive can be contained in an amount of from 0.1 to 2.5% by weight, based on the total weight of the bone cement powder. According to one embodiment, the initiator can contain dibenzoyl peroxide or can consist of dibenzoyl peroxide.

According to one embodiment, a radiopaque is understood to be a substance, which allows making the bone cement visible on diagnostic radiology images. Examples for radiopaque can include barium sulphate, zirconium dioxide, and calcium carbonate. According to one embodiment, the pharmaceutically active substance can include one or several antibiotics and optionally added Co factors for the one or the several antibiotics. The pharmaceutically active substance in one embodiment consists of one or several antibiotics and optionally added Co factors for the one or the several antibiotics. Among others, Gentamicin, Clindamycin, and Vancomycin are examples for antibiotics.

According to one embodiment, the monomer liquid can include the monomer methylmethacrylate or can consist of methylmethacrylate. In an embodiment, the monomer liquid includes, in addition to the monomer, an activator dissolved therein, such as, for example, N,N-dimethyl-p-toluidine, or consists of methylmethacrylate and N,N-dimethyl-p-toluidine.

EXAMPLES

The embodiments will be further illustrated below in an exemplary manner by using examples. The invention is not limited to the examples.

FIG. 1 illustrates a device 100 for dispensing a bone cement. The device 100 is constructed in one piece, but of several components. The device has a dispensing element 300. The dispensing element 300 is moulded in a rod-shaped manner and has an external thread 310. The external thread 310 is divided into external thread sections 320 by using axially running external thread grooves 315. The external thread grooves 315 reduce a height of an external thread flank 311 of the external thread 310 to zero. The external thread grooves 315 have a larger radial extension than the external thread sections 320. In a further, non-illustrated embodiment, the external thread grooves 315 have the same radial extension as the external thread sections 320.

At a first end 301, the dispensing element 300 has a screw means 350 in the form of a handle. The screw means 350 in the form of a handle makes it easier for the user to use the device 100, in one embodiment an axial shifting and a rotation of the dispensing element 300 about a longitudinal axis 700.

At a second end 302, the device 100 has a switching system 200, whereby the switching system 200 is arranged around the dispensing element 300 in a sleeve-like manner and can be moved axially along the entire length of the external thread 310. The switching system 200 is constructed in one piece, but of several components. The switching system 200 includes a first hollow cylinder 210 and a second hollow cylinder 250, whereby the first hollow cylinder 210 and the second hollow cylinder 250 are axially connected to one another. The first hollow cylinder 210 and the second hollow cylinder 250 can be moved against one another in a rotatory manner about the longitudinal axis 700 by using a rotational movement.

To facilitate the rotational movement of the first hollow cylinder 210 in the opposite direction against the second hollow cylinder 250 for the user of the device 100, the first hollow cylinder 210 as well as the second hollow cylinder 250 have axially running beads 280. The beads 280 improve the grip and thus increase the security against undesired slipping in the course of the rotational movement. In further, non-illustrated embodiments, the first hollow cylinder 210 and the second hollow cylinder 250 have nubs or grooves instead of the beads 280 to prevent a slipping of the user.

Due to the rotatory movement of the first hollow cylinder 210 in the opposite direction against the second hollow cylinder 250, the switching system 200 can be reversibly shifted between a first switching system position and a second switching system position. To illustrate the user whether the switching system 200 is in the first switching system position or in the second switching system position, the device 100 has optical markings 360 in the form of a notch 361 at the second hollow cylinder 250, and a first arrow 362a and a second arrow 362b at the first hollow cylinder 210. If the notches 361 and the first arrow 362a are located axially on top of one another, this indicates the setting of the switching system 200 in the first switching system position or the second switching system position to the user. An axial overlapping of the notch 361 with the second arrow 362b indicates the corresponding other switching system position to the user. In further, non-illustrated embodiments, the switching system has other types of optical markings 360, such as, for example, lines, numbers, or indentations, instead of the notch 361 and the first arrow 362a as well as the second arrow 362b.

Figure 2:
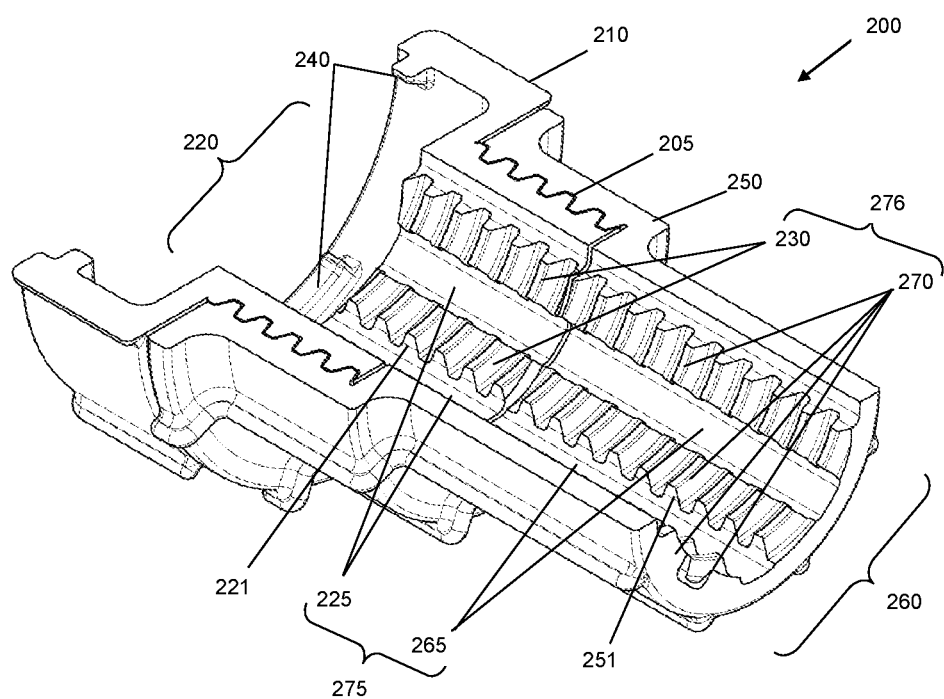
FIG. 2 illustrates a schematic cross-section of a switching system of the device from FIG. 1 in a second switching system position.

FIG. 2 illustrate a cross-section of the switching system 200 from FIG. 1. The first hollow cylinder 210 and the second hollow cylinder 250 are axially connected to one another via a threaded connection 205 in such a way that a rotational movement of the first hollow cylinder 210 in the opposite direction against the second hollow cylinder 250 can reversibly move the switching system 200 between the first switching system position and the second switching system position.

The first hollow cylinder 210 has a first internal thread 220, and the second hollow cylinder 250 has a second internal thread 260. The first internal thread 220 is divided into first internal thread sections 230 by axially running first internal thread grooves 225. The first internal thread grooves 225 reduce a height of a first internal thread flank 221 to zero. The second internal thread 260 is divided into second internal thread sections 270 by axially running second internal thread grooves 265. The second internal thread grooves 265 reduce a height of a second internal thread flank 251 to zero. The first internal thread grooves 225 have a larger radial extension than the first internal thread sections 230, and the second internal thread grooves 265 have a larger radial extension than the second internal thread sections 270. The first internal thread grooves 225 and the second internal thread grooves 265 as well as the first internal thread sections 230 and the second internal thread sections 270 each have the same radial extension. In a further, non-illustrated embodiment, the first internal thread grooves 225, the first internal thread sections 230, the second internal thread grooves 265, and the second internal thread sections 270 have the same radial extension.

In FIG. 2, the switching system 200 is illustrated in the second switching system position. In the second switching system position, the first internal thread grooves 225 and the second internal thread grooves 265 as well as the first internal thread sections 230 and the second internal thread sections 270 are arranged along axes, which run essentially jointly. Together, the first internal thread grooves 225 and the second internal thread grooves 265 thus form total internal thread grooves 275, which run over a total length of the first internal thread 220 and of the second internal thread 260, and, together, the first internal thread sections 230 and the second internal thread sections 270 form total internal thread sections 276, which run over the total length of the first internal thread 220 and of the second internal thread 260.

The total internal thread grooves 275 have a larger radial extension than the external thread sections 320 in FIG. 1, and the total internal thread sections have a smaller radial extension than the external thread grooves 315 in FIG. 1. In the second switching system position, the dispensing element 300 from FIG. 1 can thus be reversibly shifted axially against the switching system 200 by using a shifting movement. To be able to freely axially shift the dispensing element 300 from FIG. 1 against the switching system 200 in the second switching system position, the external thread sections 320 are arranged along the total internal thread grooves 275, and the external thread grooves 315 are arranged along the total internal thread sections 276.

The first hollow cylinder has a connecting element 240 in the form of a bayonet closure, by using which the device 100 can be reversibly fastened to a corresponding counter piece of a container, in one embodiment to a container, which is filled with a bone cement.

Figure 3:
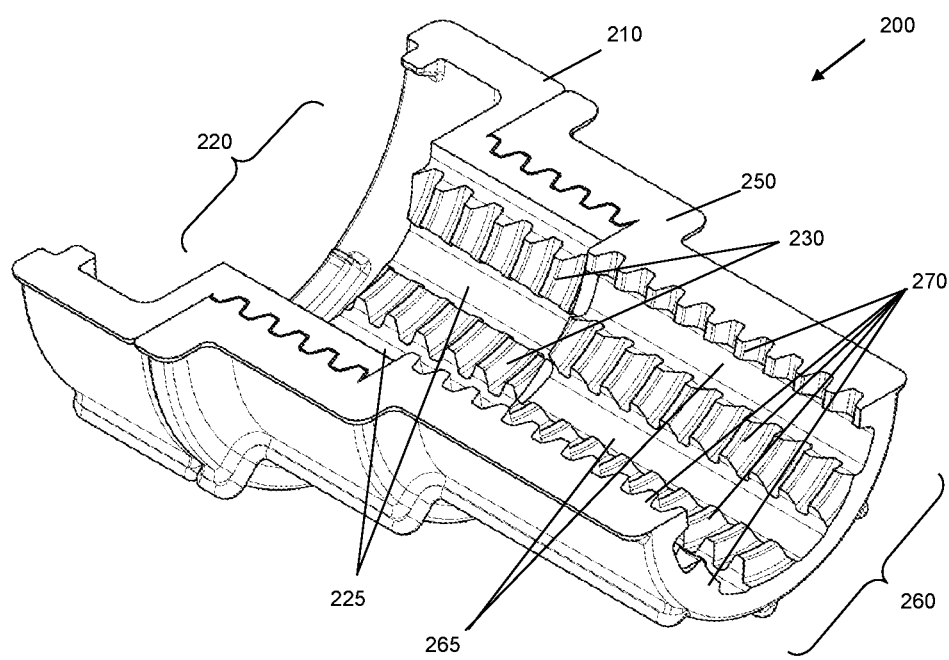
FIG. 3 illustrates a schematic cross-section of the switching system of the device from FIG. 2 in a first switching system position.

FIG. 3 illustrates the switching system 200 from FIG. 2 in the first switching system position. FIG. 2 and FIG. 3 illustrate the same switching system 200, but in different switching system positions. FIG. 2 illustrates the switching system 200 in the second switching system position, and FIG. 3 illustrates the switching system 200 in the first switching system position. The first internal thread grooves 225 and the second internal thread grooves 265, and thus also the first internal thread sections 230 and the second internal thread sections 270 are each not arranged on an essential common axis but offset to one another. In the axial extension, the first internal thread grooves 225 are located on an essentially common axis with the second internal thread sections 270, and the first internal thread sections 230 are located on an essentially common axis with the second internal thread grooves 265. In the first switching system position, it is thus not possible for the external thread sections 320 from FIG. 1 to be shifted freely axially against the switching system 200. In the first switching system position, the first internal thread 220 and the second internal thread 260 are arranged relative to one another in such a way that the external thread sections 320 from FIG. 1 cooperate in a positive and/or non-positive manner with the first internal thread sections 230 and/or the second internal thread sections 270 at any time, whereby the dispensing element 300 from FIG. 1 can only be moved against the switching system 200 by using a rotational movement.

Figure 4:
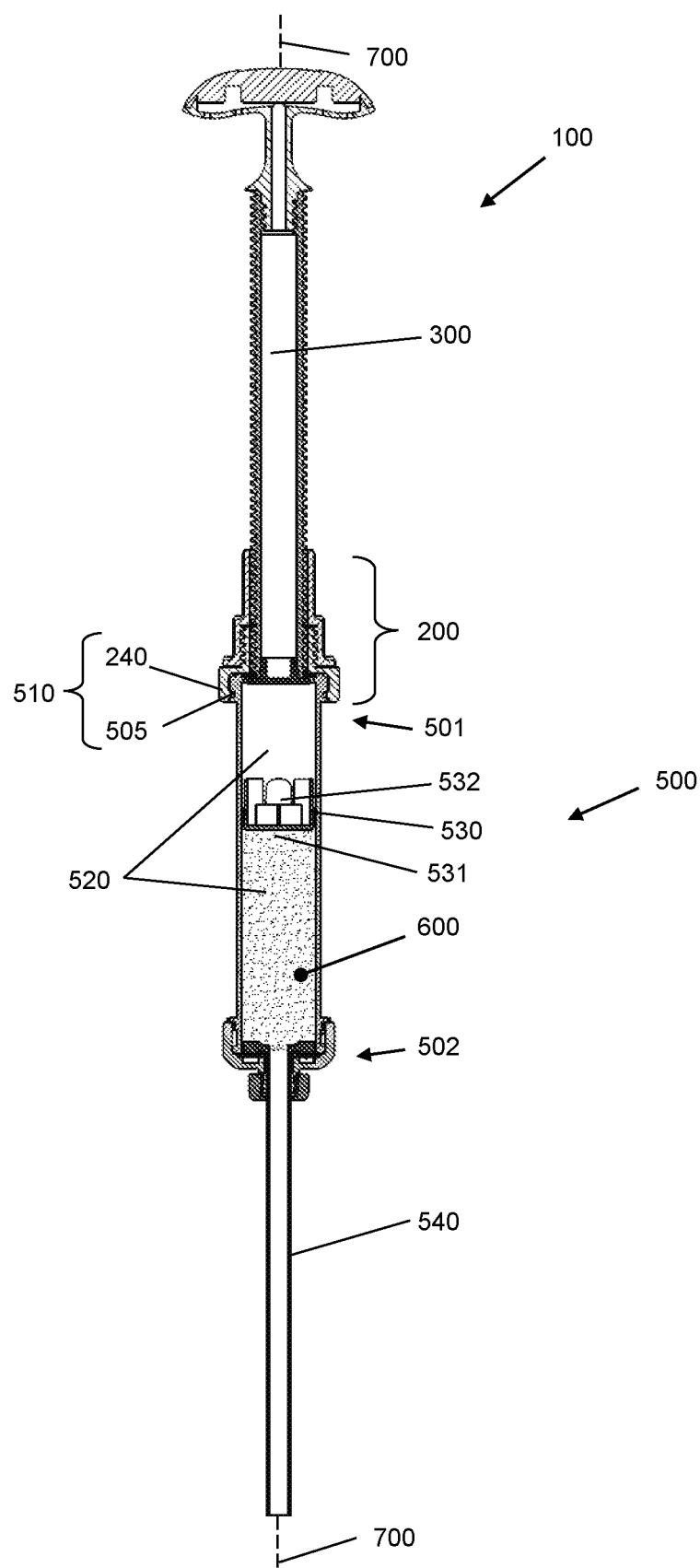
FIG. 4 illustrates a schematic cross-section of the device from FIG. 1, fastened to a container filled with a bone cement.

FIG. 4 illustrates the device 100 from FIG. 1, fastened to a first container end 501 of a container 500. The device 100 and the container 500 are reversibly connected axially to one another via the connecting element 240 and a connection 505 of the container 500. Together, the connecting element 240 and the connection 505 form a bayonet closure 510. Together, the device 100 and the container 500 are arranged on the longitudinal axis 700.

The container 500 is embodied in a tubular manner and has, in an interior 520, a bone cement 600, which is available for dispensing and for surgical purposes. To dispense the bone cement 600, the container 500 has, in an interior 520, an axially movable dispensing piston 530, which is spatially arranged between the dispensing element 300 and the bone cement 600. The dispensing piston 530 has a flat outer side 531 facing the bone cement 600 including a diameter, which essentially corresponds to an inner diameter of the container 500, and an inner side 532 facing the dispensing element 300, wherein the inner side 532 is embodied to partially receive the dispensing element in a cap-like manner. In further, non-illustrated embodiments, the outer side 531 is not formed to be flat, but for example convex or conically, and/or the inner side 532 is not moulded in a cap-like manner, but, for example, to be flat. To apply the bone cement 600 to a desired point in a specific manner, the container 500 has a dispensing spout 540 at a second container end 502 opposite the first container end 501.

The bone cement 600 can be dispensed by an introduction of the dispensing element 300 into the container 500. The manner of the introduction of the dispensing element 300 into the container 500 is controlled via the switching system 200. In the first switching system position, the dispensing element 300 can be introduced into the container 500 only by using a rotational movement, while the dispensing element 300 can be pushed freely axially into the container 500 in the second switching system position. The second switching system position thus allows for an introduction, which is quick and effortless for the user, of the dispensing element 300, in one embodiment until the dispensing element 300 is in contact with the dispensing piston 530. Due to the fact that the provided bone cement 600 can only be used for a short time, for example within a time window of up to 5 minutes after the provision, before the hardening has progressed too much, the second switching system position is preferred for the introduction of the dispensing element 300 until the contact with the dispensing piston 530. In a further, non-illustrated embodiment, in which the bone cement 600 is not already present in the container 500, collected in the direction of the dispensing spout 540, the introduction of the dispensing element 300 is preferred in the second switching system position, until the bone cement has shifted and thus collected the bone cement 600 in the direction of the dispensing spout 540 by a continued introduction of the dispensing element 300 and thus also of the dispensing piston 530, and a dispensing of the bone cement 600 through the dispensing spout 540 by using shifting movement is made more difficult due to the pasty viscosity of the bone cement 600. The same also applies for further, non-illustrated embodiments without dispensing piston 530. In embodiments without dispensing piston 530, the dispensing element 300 is embodied such that at least an end facing the bone cement 600 has an outer diameter, which essentially corresponds to an inner diameter of the container 500, whereby the dispensing element 300 itself acts as dispensing piston.

Figure 5:
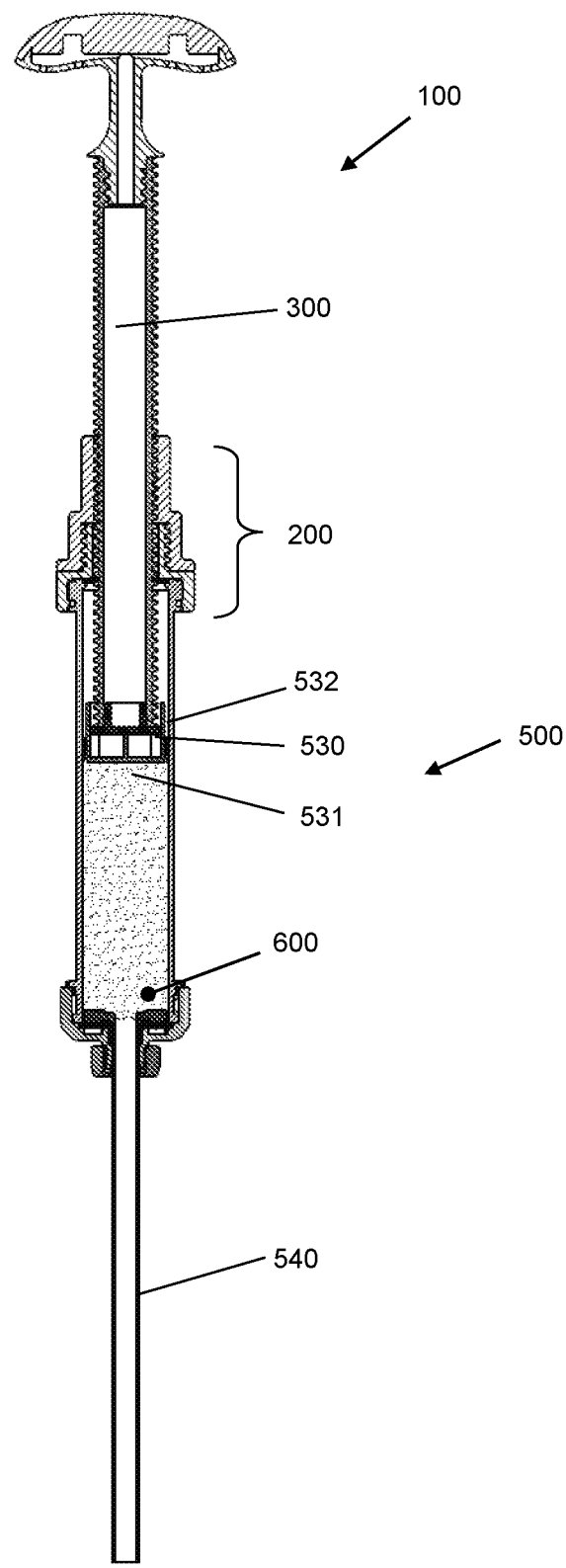
FIG. 5 illustrates the device from FIG. 4 including a dispensing element inserted into the container.

FIG. 5 illustrates the device 100 and the container 500 from FIG. 4 with dispensing element 300 introduced into the container 500. In contrast to FIG. 4, the dispensing element 300 has been brought into contact with the dispensing piston 530, in one embodiment with the cover-like inner side 532, whereby the dispensing piston 530 has not yet been shifted in the direction of the dispensing spout 540, and the dispensing of the bone cement 600 from the container 500 has thus not yet begun. Due to the pasty viscosity and the cross-sectional surface of the dispensing spout 540, which is reduced as compared to the container 500, a continued introduction of the dispensing element 300 into the container 500 leads to an increased force from the user. In the case of the arrangement of the dispensing element 300 illustrated in FIG. 5, it is thus preferred to move the switching system 200 from the second switching system position into the first switching system position. The dispensing element 300 can thus no longer be inserted freely axially into the container by using shifting movement, but the external thread sections 320 from FIG. 1 cooperate in a positive and/or non-positive manner with the first internal thread sections 230 and/or the second internal thread sections 270 from FIG. 3. The dispensing element 300 can thus be introduced further into the container 500 only via a rotation movement, which, on the one hand, reduces the required force from the user, and furthermore provides for a more exact metering of the bone cement 600 than in the case of a shifting movement, which is difficult to control.

Figure 6:
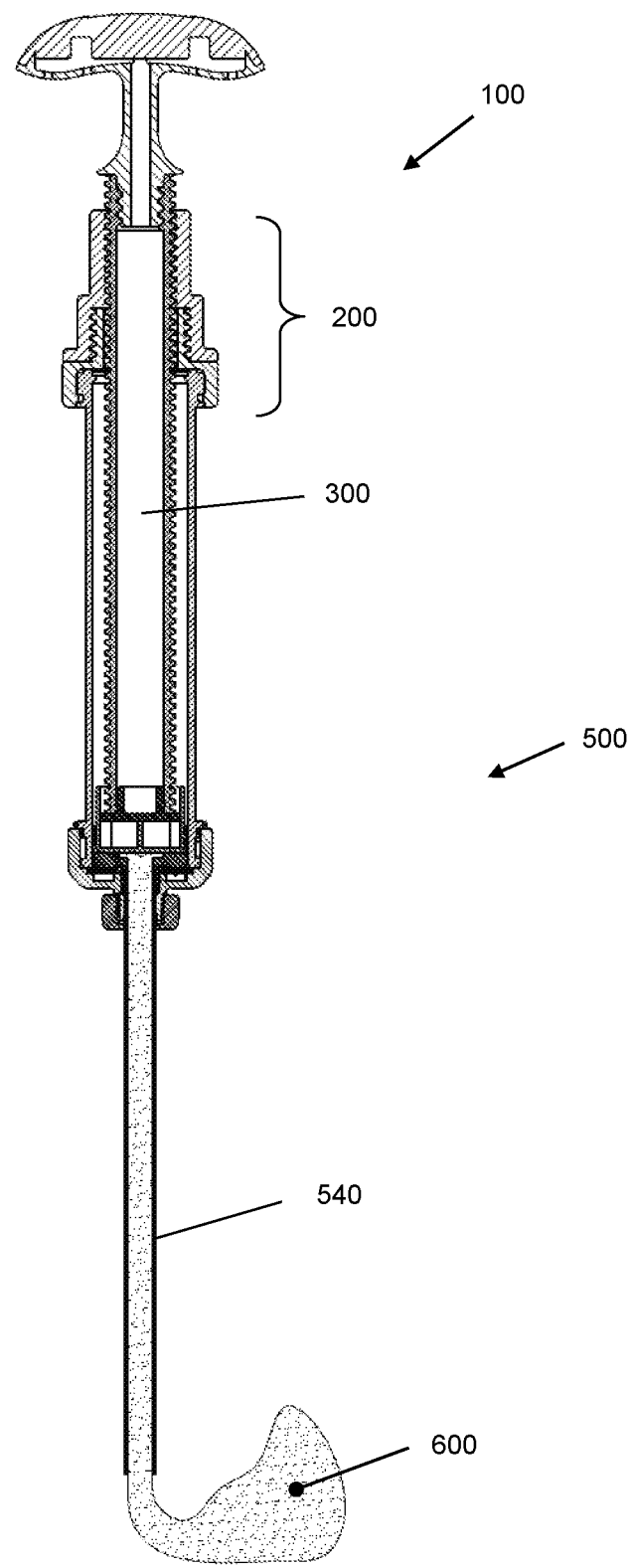
FIG. 6 illustrates the device from FIG. 5 after a dispensing of the bone cement from the container.

FIG. 6 illustrates the device 100 and the container 500 from FIG. 5 after dispensing of the bone cement 600 has taken place. The dispensing element 300 has been inserted, in one embodiment screwed, as far as possible into the container 500. The bone cement 600 has been dispensed completely from the container 500 at the desired point, whereby the dispensing spout 540 is filled with residues of the bone cement 600.

Figure 7:
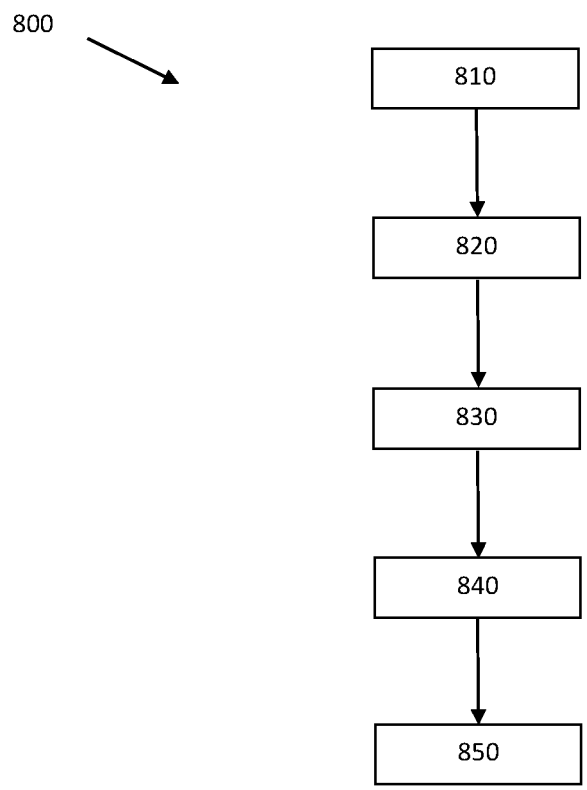
FIG. 7 illustrates a method for dispensing a bone cement from a container by using a device.

FIG. 7 illustrates a flowchart containing steps 810 to 850 of a method 800 for dispensing a bone cement 600 from a container 500 by using the device 100 including the connecting element 240 for reversibly connecting the device 100 to the container 500, the rod-like dispensing element 300, which at least partially has the external thread 310, the switching system 200, which at least partially has the first internal thread 220, wherein the first internal thread 220 can be coupled in a positive manner to the external thread 310 in such a way that the dispensing element 300 can be axially screwed into the container 500 in the first coupled switching system position, and the dispensing element 300 can be pushed freely axially into the container 500 in the second decoupled switching system position. In a preferred embodiment, the dispensing piston 530 is supported between the dispensing element 300 and the bone cement 600 within the container 500.

In a step 810, the device 100 is reversibly connected axially to the container 500 by using the connecting element 240. The connecting element 240 in one embodiment forms the bayonet closure 510 with the container 500, in order to reversibly connect the device 100 to the container 500.

In a further step 820, the switching system 200 is moved into the second switching system position, so that the dispensing element can be inserted freely axially into the container 500. In an embodiment of the method 800, the connecting of the device 100 to the container 500 in step 810 takes place prior to step 820. In a further embodiment of the method 800, the switching system 200 was moved into the second switching system position prior to step 810.

In a further step 830, the dispensing element 300 is inserted freely axially into the container 500. The dispensing element 300 is in one embodiment inserted into the container until the user experiences a significant resistance against the pushing movement. This resistance can appear, for example, in response to contact with the dispensing piston 530 or with the onset of the movement of the bone cement from the container 500 into the dispensing spout 540. An advantage of the free axial insertion of the dispensing element 300 into the container 500 is the quick performability of step 820. This is important in one embodiment as part of time-critical surgeries and because the bone cement 600 only has a short time period, for example of up to 5 minutes, for being moved to the desired point prior to the hardening as a function of the chemical composition.

If the dispensing element 300 is inserted into the container 500 all the way to the desired point, the switching system 200 is moved into the first switching system position by using a rotatory movement about the longitudinal axis 700 of the dispensing element in a further step 840. In the first switching system position, the dispensing element 300 can no longer be inserted freely axially into the first container but can only be further introduced via a rotational movement. The movement of the switching system 200 from the second switching system position into the first switching system position is possible by using a further rotary movement opposite to the rotatory movement. An advantage of moving the switching system 200 from the second switching system position into the first switching system position by using a rotatory movement is that the user of the device 100 has both hands free again for further operating the device 100 or further surgical objects after switchover has taken place. The switching system 200 independently remains in the selected switching system position, until the user becomes active again.

In a preferred embodiment of the method 800, the reversible moving of the switching system 200 into the first switching system position and the second switching system position takes place by using a rotatory movement of the first hollow cylinder 210 in the opposite direction against the second hollow cylinder 250 about the longitudinal axis 700 of the dispensing element 300. The rotatory movement in the opposite direction moves the at least one first internal thread groove 225 of the first internal thread 220, which runs along the longitudinal axis, and the at least one second internal thread groove 265 of the second internal thread 260 to a common axis. In the second switching system position, the at least one first internal thread groove 225 and the at least one second internal thread groove 265 form the total internal thread groove 275, which runs essentially in a straight line. If the external thread sections 320 of the external thread 310 are arranged along the essentially identical axis as the total internal thread groove 275, the dispensing element 300 can be inserted freely axially into the container 500 in step 830. A further rotatory movement into the first switching system position moves the first internal thread groove 225 against the second internal thread groove 265 out of the essentially common axis, whereby the external thread sections 320 can no longer be shifted freely axially, but instead cooperate in a positive and/or non-positive manner with the first internal thread sections 230 and/or the second internal thread sections 270.

In the first switching system position, this provides for a screw-in of the dispensing element 300 into the container 500.

In a further step 850, the bone cement 600 is dispensed from the container 500 by screwing the dispensing element 300 into the container 500. The dispensing element 300 is thereby screwed into the container 500 until the desired amount of bone cement 600 has been applied. The screw-in additionally makes it easer for the user to dispense the pasty bone cement 600 as compared to the insertion of the dispensing element 300.

The features disclosed in the claims, the description, and in the figures can be essential for various embodiments of the claimed embodiments, both separately and in any combination with one another. The features disclosed for the device are also disclosed for the method and vice versa.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A device for dispensing a bone cement from a container, comprising:
   a connecting element for connecting and disconnecting the device to the container;
   a dispensing element, which has an external thread;
   a switching system, which has a first internal thread;
   wherein the first internal thread can be coupled in a positive manner to the external thread in such a way that the dispensing element can be axially screwed into the container in a first coupled switching system position and the dispensing element can be pushed freely axially into the container in a second decoupled switching system position;
   wherein the first internal thread encompasses the dispensing element, and the switching system can be reversibly shifted between the first switching system position and the second switching system position by a rotatory movement about a longitudinal axis of the dispensing element;
   wherein the switching system has a first hollow cylinder, which has the first internal thread, and a second hollow cylinder, which is axially connected to the first hollow cylinder; and
   wherein the first hollow cylinder and the second hollow cylinder are connected in such a way that the switching system can be reversibly shifted between the first switching system position and the second switching system position by a rotatory movement of the first hollow cylinder in the opposite direction against the second hollow cylinder about the longitudinal axis.

2. The device according to claim 1, wherein the second hollow cylinder has a second internal thread, and the external thread has an external thread groove, which runs along the longitudinal axis;
   the first internal thread has a first internal thread groove, which runs along the longitudinal axis; and
   the second internal thread has a second internal thread groove, which runs along the longitudinal axis.

3. The device according to claim 2, wherein the external thread groove divides the external thread into external thread sections;
   the first internal thread groove divides the first internal thread into first internal thread sections, and the second internal thread groove divides the second internal thread into second internal thread sections along the longitudinal axis.

4. The device according to claim 3, wherein a radial extension of the external thread groove, of the first internal thread groove, and of the second internal thread groove, is equal to or larger than a radial extension of the external thread section, of the first internal thread section, and of the second internal thread section.

5. The device according to claim 2, wherein the external thread, the first internal thread, and the second internal thread are aligned.

6. The device according to claim 2, wherein the external thread, the first internal thread, and the second internal thread each have an identical number of external thread grooves, first internal thread grooves, and second internal thread grooves.

7. The device according to claim 2, wherein the first internal thread groove and the second internal thread groove are located on an essentially common axis in the second switching system position.

8. The device according to claim 7, wherein the first internal thread groove and the second internal thread groove are oriented to the external thread, in particular are located on a common axis, in such a way in the second switching system position that the external thread can be pushed axially freely into the first internal thread groove and the second internal thread groove, in order to push the dispensing element freely axially into the container.

9. The device according to claim 2, wherein the first internal thread groove and the second internal thread groove are not located on a common axis in the first switching system position.

10. The device according to claim 9, wherein the first internal thread groove and the second internal thread groove are not located on a common axis in the first switching system position, so that the external thread couples to one another with the first internal thread and the second internal thread in such a way that the dispensing element can be screwed axially into the container.

11. The device according to claim 1, wherein the device is made of a compostable plastic, of a glass fibre-reinforced plastic, metal, or of a combination of compostable plastic, of a glass fibre-reinforced plastic and metal.

12. The device according to claim 1, wherein a first hollow cylinder encompasses the connecting element.

13. A method for dispensing a bone cement from a container using a device comprising:
  a connecting element for reversibly connecting the device to the container,
  a dispensing element, which has an external thread,
  a switching system, which has a first internal thread,
  wherein the first internal thread can be coupled in a positive manner to the external thread in such a way that the dispensing element can be axially screwed into the container in a first coupled switching system position, and the dispensing element can be pushed freely axially into the container in a second decoupled switching system position;
the method further comprising:
  a) connecting the device to the container by the connecting element;
  b) moving the switching system into the second switching system position;
  c) axial shifting of the dispensing element into the container;
  d) moving the switching system into the first switching system position by a rotary movement about a longitudinal axis of the dispensing element;
  e) dispensing the bone cement from the container by screwing the dispensing element into the container; and
wherein the first hollow cylinder has the first internal thread, and the second hollow cylinder has a second internal thread,
  wherein the external thread comprises an external thread groove,
  the first internal thread comprises a first internal thread groove, and
  the second internal thread comprises a second internal thread groove, and
  the external thread groove divides the external thread into external thread sections,
  the first internal thread groove divides the first internal thread into first internal thread sections, and
  the second internal thread groove divides the second internal thread into second internal thread sections, each along the longitudinal axis, and
  wherein the first internal thread groove and the second internal thread groove are arranged on an essentially common axis in the second switching system position, so that the external thread sections are shifted into the container along the common axis in step c).

14. The method according to claim 13, wherein the rotatory movement in d) shifts a first hollow cylinder of the switching system against a second hollow cylinder of the switching system in a rotatory manner.

* * * * *